(12) United States Patent
Umapathy et al.

(10) Patent No.: US 11,002,681 B2
(45) Date of Patent: May 11, 2021

(54) METHOD FOR RAPID RAMAN SPECTRA DETECTION OF A SINGLE BACTERIUM OR GROUP OF BACTERIAL SPECIES

(71) Applicant: INDIAN INSTITUTE OF SCIENCE, Bangalore (IN)

(72) Inventors: Siva Umapathy, Bangalore (IN); Deepak Kumar Saini, Bangalore (IN); Srividya Kumar, Bangalore (IN)

(73) Assignee: INDIAN INSTITUTE OF SCIENCE, Bangalore (IN)

( * ) Notice: Subject to any disclaimer, the term of this patent is extended or adjusted under 35 U.S.C. 154(b) by 0 days.

(21) Appl. No.: 15/781,150

(22) PCT Filed: Jan. 27, 2016

(86) PCT No.: PCT/IN2016/000028
§ 371 (c)(1),
(2) Date: Jun. 4, 2018

(87) PCT Pub. No.: WO2017/094019
PCT Pub. Date: Jun. 8, 2017

(65) Prior Publication Data
US 2018/0372643 A1    Dec. 27, 2018

(30) Foreign Application Priority Data

Dec. 2, 2015   (IN) .......................... 6468/CHE/2015

(51) Int. Cl.
  *G01N 21/65*   (2006.01)
  *G01N 21/94*   (2006.01)
  *C12Q 1/04*   (2006.01)
  *G01N 1/34*   (2006.01)
  *G01N 33/18*   (2006.01)

(52) U.S. Cl.
  CPC ............... *G01N 21/65* (2013.01); *C12Q 1/04* (2013.01); *G01N 1/34* (2013.01); *G01N 21/94* (2013.01); *G01N 33/1826* (2013.01)

(58) Field of Classification Search
  CPC .......... G01N 21/65; G01N 21/94; G01N 1/34; G01N 33/1826; C12Q 1/04
  See application file for complete search history.

(56) References Cited

U.S. PATENT DOCUMENTS

| | | | |
|---|---|---|---|
| 7,713,914 B2 | 5/2010 | Farquharson et al. | |
| 7,760,354 B2 | 7/2010 | Grun et al. | |
| 2004/0021860 A1 | 2/2004 | Gardner, Jr. et al. | |
| 2004/0150818 A1* | 8/2004 | Armstrong ............. | B82Y 10/00 356/301 |

(Continued)

*Primary Examiner* — Michael P LaPage
(74) *Attorney, Agent, or Firm* — Mark M. Friedman

(57) ABSTRACT

The invention provides a method for rapid detection of a specific bacterial species. The method includes preparing a sample, irradiating the prepared sample with an electromagnetic radiation of specific wavelength, capturing the electromagnetic radiation scattered by the sample to obtain a Raman spectra and analyzing the Raman spectra to obtain a unique biochemical signature. The unique biochemical signature identifies a single bacterium within the sample. The method also provides for rapid detection of a group of bacterial species within the sample. The method takes about 1 minute to about 1 hour for the detection of specific bacterial species.

8 Claims, 5 Drawing Sheets

(56) References Cited

U.S. PATENT DOCUMENTS

| | | | |
|---|---|---|---|
| 2006/0275310 A1* | 12/2006 | Dwarakanath | G01N 21/6428 424/164.1 |
| 2007/0134733 A1* | 6/2007 | Haddach | G01N 21/65 435/7.2 |
| 2007/0145249 A1* | 6/2007 | Kiesel | G01N 21/05 250/221 |
| 2007/0178067 A1 | 8/2007 | Maier et al. | |
| 2008/0151223 A1 | 6/2008 | Treado et al. | |
| 2010/0241357 A1* | 9/2010 | Chan | G01J 3/44 702/19 |
| 2011/0007309 A1* | 1/2011 | Stewart | G01N 33/1826 356/301 |
| 2011/0144212 A1* | 6/2011 | Subbaraju | A61P 39/06 514/720 |
| 2011/0184654 A1 | 7/2011 | Ben-David et al. | |
| 2011/0267614 A1 | 11/2011 | Reinhard et al. | |
| 2012/0156716 A1 | 6/2012 | Walsh et al. | |
| 2013/0040283 A1* | 2/2013 | Star | G01N 27/127 435/5 |
| 2013/0079413 A1* | 3/2013 | Hormann | A61P 37/06 514/615 |
| 2013/0157254 A1 | 6/2013 | Sengupta et al. | |
| 2016/0011117 A1* | 1/2016 | Strola | G01N 21/01 356/338 |

* cited by examiner

| Actual → Predicted ↓ | E.Coli | B.Subtilis | K.Pneumonia | M.smegmatis | M.vaccae | M.bovis |
|---|---|---|---|---|---|---|
| E.Coli | 43 | 0 | 0 | 0 | 0 | 0 |
| B.Subtilis | 0 | 32 | 0 | 0 | 0 | 0 |
| K.Pneumonia | 0 | 0 | 58 | 0 | 0 | 0 |
| M.smegmatis | 0 | 0 | 0 | 43 | 0 | 0 |
| M.vaccae | 0 | 0 | 0 | 0 | 55 | 0 |
| M.bovis | 0 | 0 | 0 | 0 | 0 | 33 |

FIG. 4a

| Actual → / Predicted ↓ | E.Coli | B.Subtilis | K.Pneumonia | M.Smegmatis | M.Vaccae | M.Bovis |
|---|---|---|---|---|---|---|
| E.Coli | 41 | 0 | 0 | 0 | 0 | 0 |
| B.Subtilis | 2 | 31 | 0 | 1 | 1 | 0 |
| K.Pneumonia | 0 | 1 | 58 | 0 | 1 | 0 |
| M.smegmatis | 0 | 0 | 0 | 42 | 0 | 3 |
| M.vaccae | 0 | 0 | 0 | 0 | 53 | 0 |
| M.bovis | 0 | 0 | 0 | 0 | 0 | 30 |

FIG. 4b

METHOD FOR RAPID RAMAN SPECTRA DETECTION OF A SINGLE BACTERIUM OR GROUP OF BACTERIAL SPECIES

FIELD OF INVENTION

The invention generally relates to the field of physical chemistry and diagnostic microbiology and particularly to a method for detection of a single bacterium or a group of bacterial species within a sample.

BACKGROUND

A variety of diagnostic methods are available in the art for detection and identification of bacterial species in any given biological sample. Examples of sample include but are not limited to those obtained from infectious diseases, food and dairy products. Examples of infectious diseases include but are not limited to pneumonia, tuberculosis, septicaemia, meningitis, urinary tract infection and gastro-intestinal infections. The existing methods are broadly classified as invasive methods and non-invasive methods. Invasive method requires rupturing or lysis of biological material in order to extract a particular biological component for identification. On the other hand, non-invasive methods do not require rupturing or lysis of the biological material.

The diagnostic methods available in the art include but are not limited to DNA/protein based methods, culturing based methods, staining based methods and mass spectrometry based methods.

DNA based methods use specific DNA sequences present in various pathogens as signatures for identification. Examples of DNA based techniques include but are not limited to PCR, RT-PCR and probe hybridization such as molecular beacons. One of the significant disadvantage of the technique is extensive sample processing and preparation steps. Another disadvantage of the technique is the requirement of specific probes for diagnosis.

Culturing based methods require inoculation of the growth medium with the biological sample containing pathogen. The bacterial colonies grown on the growth medium are then identified. The techniques of identification includes but are not limited to staining, antibiotic selection and metabolic reactions.

One significant disadvantage of the technique is elaborate procedures involved to perform the test. Another disadvantage is time required for completion of the diagnosis, which normally requires 3-4 days but may extend up to 21 days to detect a certain bacteria.

Staining and microscopy base methods use specific chemical dyes or fluorescent probes with unique chemistry to stain and visualize various bacterial species. The technique allows species identification by differential staining analysis. Some disadvantages of the technique are requirement of skilled persons and has limited potential for low bacterial loads specially for single bacterial identification.

Mass spectrometry uses a mass spectrometer to analyse extracted DNA or RNA or protein or lipids or other biological molecules. The mass signatures obtained are analyzed for bacterial species identification. Limitation of the technique is that it has a poor application as a stand-alone technique for single bacterial identification and is often used along with PCR.

Thus there is a need for a diagnostic method that has high specificity and sensitivity and is less time consuming.

BRIEF DESCRIPTION OF DRAWINGS

So that the manner in which the recited features of the invention can be understood in detail, some of the embodiments are illustrated in the appended drawings. It is to be noted, however, that the appended drawings illustrate only typical embodiments of this invention and are therefore not to be considered limiting is of its scope, for the invention may admit to other equally effective embodiments.

FIG. 4a shows an confusion matrix obtained for predicting the efficiency and reliability of the detection method, according to one example of the invention.

FIG. 4b shows a confusion matrix for predicting the efficiency of the detection method, according to another example of the invention.

SUMMARY OF THE INVENTION

Figure 1:
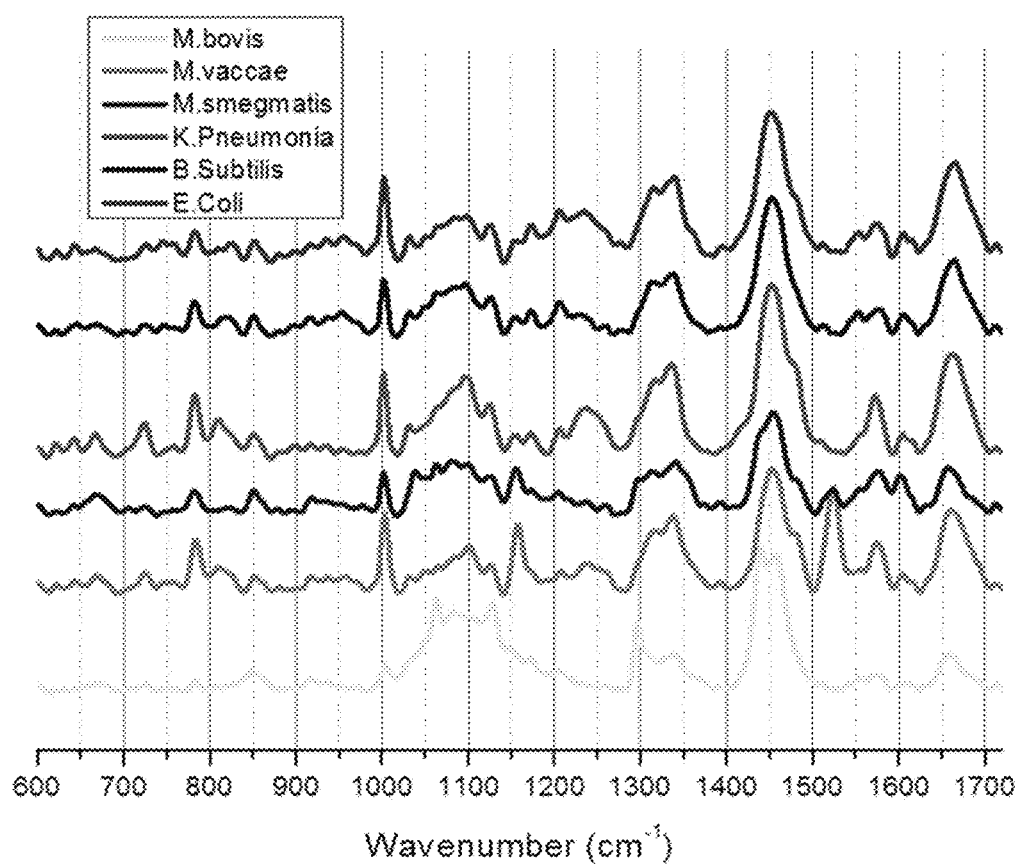
FIG. 1 shows an averaged Raman spectra obtained from various kinds of bacteria at lower wave number region, according to an embodiment of the invention.

One aspect of the invention provides a method for rapid detection of a single bacterium within a sample. The method includes preparing a sample, irradiating the prepared sample with an electromagnetic radiation of specific wavelength, capturing the electromagnetic radiation scattered by the sample to obtain a Raman spectra and analyzing the Raman spectra to obtain a unique biochemical signature. The unique biochemical signature obtained identifies the single bacterium within the sample.

Another aspect of the invention provides a method for rapid detection of a group of a bacterial species within a sample. Yet another aspect of the invention provides a method for preparation of a substrate for casting the sample. The method includes selecting a silicon wafer and depositing a metal layer on the silicon wafer.

DETAILED DESCRIPTION OF THE INVENTION

Various embodiments of the invention provide a method for detection of a single bacterium within a sample. The method includes preparing a sample, irradiating the prepared sample with an electromagnetic radiation of specific wavelength, capturing the electromagnetic radiation scattered by the sample to obtain a Raman spectra and analyzing the Raman spectra to obtain a unique biochemical signature. The unique biochemical signature obtained identifies the single bacterium within the sample.

The method also includes, preparing a sample, irradiating the prepared sample with an electromagnetic radiation of specific wavelength, capturing the electromagnetic radiation scattered by the sample to obtain a Raman spectra and analyzing the Raman spectra to obtain a unique biochemical signature. The unique biochemical signature obtained identifies a group of bacterial species within the sample.

The method of rapid detection is based on Raman microspecrometry. Raman microspectrometry uses Raman spectrometry to measure the spectra of microscopic samples. A Raman microspectrometer is used which allows acquisition of Raman spectra of microscopic samples. The technique captures molecular bond specific vibrations originating from the biochemical constituents of the cell. The spatial resolution required for single bacterial biochemical fingerprint is achieved with the use of microscopy along with the spectroscopy.

The method described in brief hereinabove shall be described in details with various embodiments. The method involves the steps of preparing a sample, irradiating the sample with an electromagnetic radiation of specific wavelength, capturing the electromagnetic radiation scattered by the sample to obtain a Raman spectra and analysing the Raman spectra to obtain, a unique biochemical signature. The unique biochemical signature obtained identifies a single or group of bacterial species within the sample.

First step for detection is preparation of a sample. The sample used for detection includes but is not limited to a body fluid sample, a tissue sample, a food sample. Sample preparation is done by first decontaminating the sample. Decontamination is achieved by irradiation or by heat or by chemical treatment. The decontaminated sample is then washed three times with autoclaved Type1 water. Washing is done to remove lysed cellular components. The washed and decontaminated sample is then dried and casted on a substrate. In one embodiment of the invention, prior to casting on the substrate, the decontaminated cells in the sample are fixed by using paraformaldehyde solution.

The substrate is fabricated by depositing a layer of metal on a silicon wafer. The deposition of the metal layer is achieved by first sputter coating and then annealing the metal on the silicon wafer. The thickness of the metal layer is in the range of 100 nm to 1 mm. Examples of metal include but are not limited to aluminium, silver and gold. In one embodiment of the invention, aluminium is deposited on the silicon wafer. The prepared sample is then irradiated with an electromagnetic radiation. The wavelength of the electromagnetic radiation is in the range of 200 nm to 1400 nm. In, one example of the invention, the source of electromagnetic radiation is a laser source. For irradiation, electromagnetic radiation from a radiation source is focused through a plurality of mirrors and lenses or a microscopic objective on the prepared sample. The electromagnetic radiation scattered by the sample is then dispersed using a grating. The dispersed electromagnetic radiation is then captured by a detector and a Raman spectra is obtained. The Raman spectra obtained is molecular bond specific and represents biochemical composition of the bacterial species. The Raman spectra obtained is then analysed to obtain biochemical signatures specific to the bacterial species. The resolution of the Raman spectra obtained is in the range of 1 $cm^{-1}$ to 8 $cm^{-1}$. Further, the time duration for identification of the bacterium is in the range of one minute to 1 hour.

Identification and Validation:

Six bacterial species namely *E. coli* (gram negative, aerobic), *B. subtilis* (gram positive, aerobic), *K. pneumoniae* (gram negative, aerobic), *M. smegmatis* (gram positive, aerobic), *M. vaccae* (gram positive, aerobic) and *M. bovis* (gram positive, aerobic) are cultured. The cultured bacteria are harvested and pelleted by centrifugation at 5000 g for 5 minutes. The pelleted bacteria are then washed thrice with autoclaved Type 1 water. After washing the bacteria are dry casted on the substrate.

The substrate is fabricated by first sputter coating and then annealing aluminium as a 200 nm layer on a silicon wafer. The dry-casted bacterial sample are then mounted on a microscope, focused to the appropriate location and then irradiated by a laser source having a wavelength of 633 nm. The electromagnetic radiation scattered by the bacterial sample are focused and collected using a 100×, 0.8NA objective. The scattered radiation after passing the notch filter is focussed on to a monochromator with 1200 lines/mm grating and detected using a Peltier cooled CCD camera at 256×1048 pixels resolution.

During spectroscopic evaluation, for the lower wave number region 500-1900 $cm^{-1}$ the bacteria are exposed for 15 seconds and the spectra is accumulated 5 times to get a good signal to noise ratio. For the higher wave number region 2800-3000 $cm^{-1}$ the bacteria are exposed for 10 seconds and the spectra is accumulated three times. After data collection, the spectra is subjected to pre-processing which included, cosmic ray removal, multipoint base line correction, Savitzky-Golay smoothing and vector normalization using Renishaw wire 4.2 and OriginPro 8.5 software. The averaged data is used for univariate analysis and the complete dataset after pre-processing is used for multivariate analysis.

Figure 2:
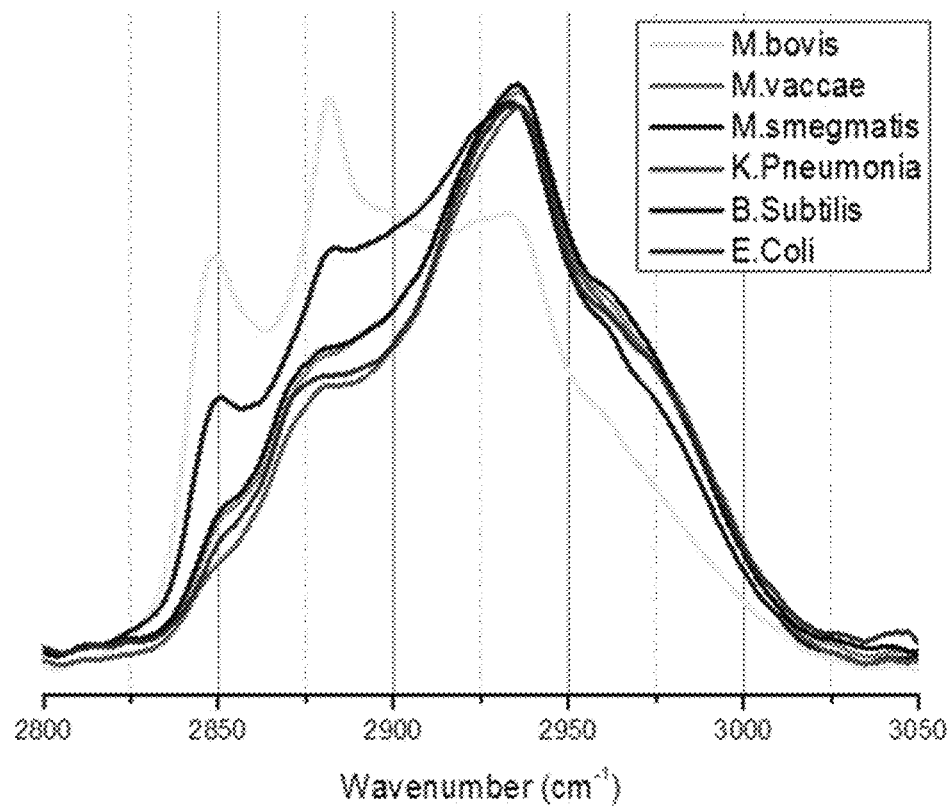
FIG. 2 shows an averaged Raman spectra obtained from various kinds of bacteria at higher wave number region, according to an embodiment of the invention.

FIG. 1 and FIG. 2 generally shows averaged Raman spectra obtained from various kinds of bacteria at lower wave number region and at higher wave number region, respectively. The figures show that at both lower wave number region and higher wave number region, various kind of bacteria exhibit distinctly different spectra from one another. The spectra of *M. bovis* clearly reflects the fact that the main discriminatory features are dominated by peaks pertaining to lipids and mycolic acids in their cell wall compared to other five strains. Similarly, *M. vaccae* exhibit distinct spectra because of presence of carotenoids. In *M. smegmatis* comparatively lesser amount of carotenoids is detected but the higher region suggest that these are also rich in lipids. *E. coli* and *B. subtilis* being gram negative control bacteria and gram positive control bacteria, respectively, yield distinct signatures showing complete demarcation from Mycobacterial species.

Figure 3:
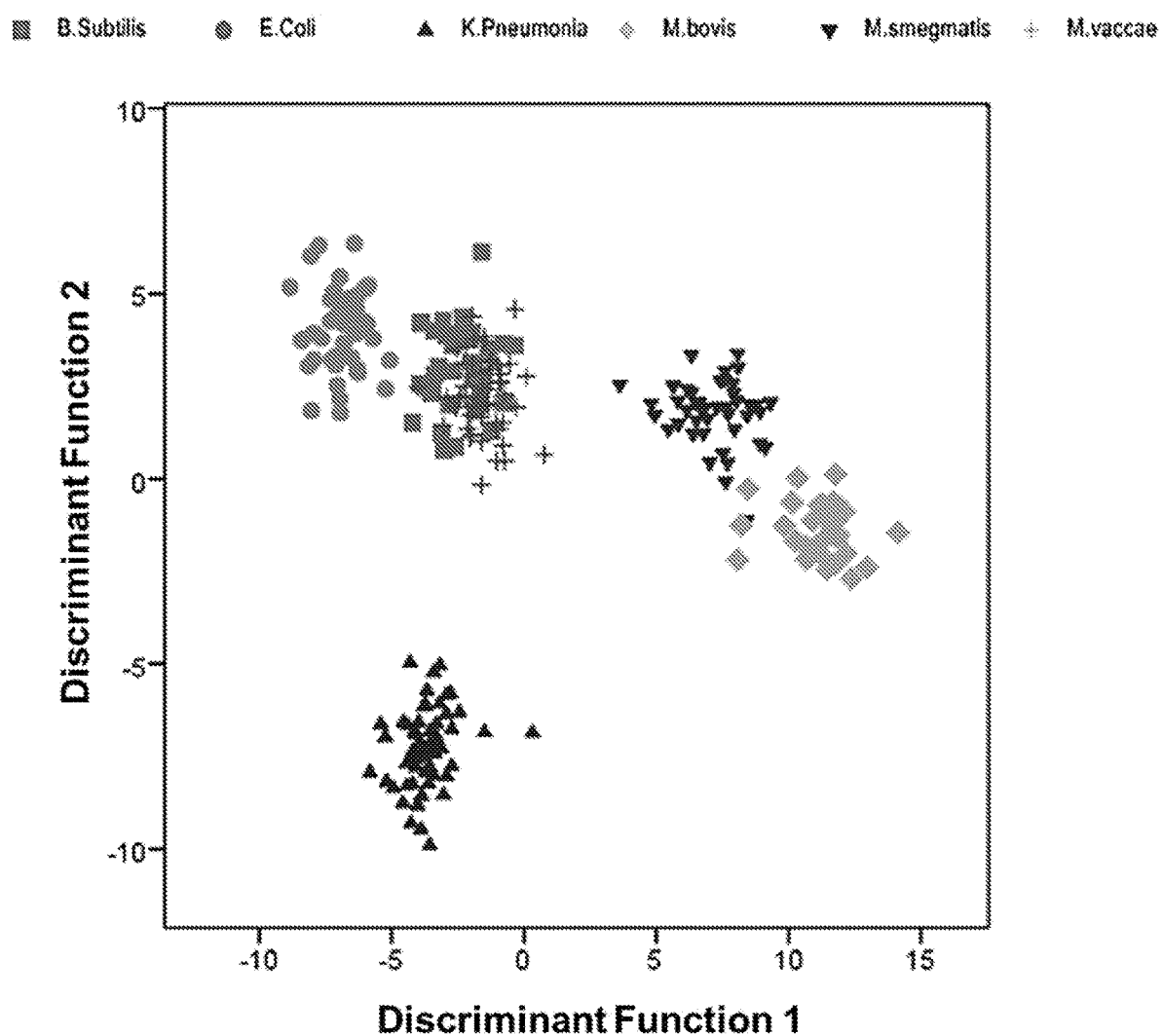
FIG. 3 shows a 2D scatter plot obtained from a PC-Linear Discriminant Analysis of the spectra of various kinds of bacteria, according to one example of the invention.

FIG. 3 shows a 2D scatter plot obtained from a PC-Linear Discriminant Analysis of the spectra of various kinds of bacteria, according to one example of the invention. Each point in the plot denotes the complete spectrum. Each spectrum is colour coded to their respective kind of bacteria, as is evident that the points of same colour cluster together.

FIG. 4a shows an confusion matrix obtained for predicting the efficiency and reliability of the detection method, according to one example of the invention. The confusion matrix reveals that the actual values of all the spectra collected are correctly predicted to their respective sources, i.e. actual values perfectly matches the predicted values. When the number of components used by the LDA is reduced, for example to 6 components the accuracy came down to 96.5% as indicated by FIG. 4b that shows an confusion matrix obtained for predicting the efficiency and reliability of the detection method, according to another example of the invention.

The invention thus provides a method for rapid detection of a single bacterium within a sample. The sample preparation technique provided in the invention do not involve culturing or staining which are time consuming. Thus, the method provides for early and accurate detection of bacterial species in infectious disease and in food contamination even at low bacterial load.

Thus the method can be used as a potential diagnostic tool for rapid detection of bacteria in infectious diseases, in food contamination and in water contamination.

The foregoing description of the invention has been set merely to illustrate the invention and is not intended to be limiting. Since modifications of the disclosed embodiments incorporating the spirit and substance of the invention may occur to person skilled in the art, the invention should be construed to include everything within the scope of the appended claims and equivalents thereof.

We claim:

1. A method for detecting a single bacterium within a sample, comprising:
    preparing the sample including:
        decontaminating the sample;
        removing lysed cellular components from the decontaminated sample; and,
        casting the decontaminated sample on a substrate, wherein said casting is achieved by selecting a silicon wafer, sputter coating an aluminum layer having a thickness in the range of 100 nm to 1 mm on the silicon wafer, and annealing the sputter coated aluminum layer on the silicon wafer;
    irradiating the sample with an electromagnetic radiation of a wavelength in the range of 200 nm to 1400 nm;
    capturing the electromagnetic radiation scattered by the sample to obtain a Raman spectra, wherein the resolution of the Raman spectra is in the range of 1 cm-1 to 8 cm-1; and,
    analyzing the Raman spectra to obtain a unique biochemical signature, wherein the biochemical signature is molecular bond specific;
    wherein the unique biochemical signature obtained identifies the single bacterium.

2. The method of claim 1, wherein the bacterium is selected from a group consisting of a gram positive bacteria, a gram negative bacteria, an aerobic bacteria, an anaerobic bacteria and a mycobacteria.

3. The method of claim 1, wherein the sample is selected from a group consisting of a body fluid sample, a tissue sample, a food sample.

4. The method of claim 1, wherein the bacterium is detected within a time period ranging from about one minute to about one hour.

5. A method for detecting a group of bacterial species within a sample comprising:
    preparing the sample including:
        decontaminating the sample;
        removing lysed cellular components from the decontaminated sample;
    and, casting the decontaminated sample on a substrate, wherein said casting is achieved by selecting a silicon wafer, sputter coating an aluminum layer having a thickness in the range of 100 nm to 1 mm on the silicon wafer, and annealing the sputter coated aluminum layer on the silicon wafer;
    irradiating the sample with an electromagnetic radiation of a wavelength in the range of 200 nm to 1400 nm;
    capturing the electromagnetic radiation scattered by the sample to obtain a Raman spectra, wherein the resolution of the Raman spectra is in the range of 1 cm-1 to 8 cm-1; and,
    analyzing the Raman spectra to obtain a unique biochemical signature,
    wherein the biochemical signature is molecular bond specific;
    wherein the unique biochemical signatures obtained identifies a group of bacterial species.

6. The method of claim 5, wherein the bacterial species is selected from a group consisting of a gram positive bacteria, a gram negative bacteria, an aerobic bacteria, an anaerobic bacteria and a mycobacteria.

7. The method of claim 5, wherein the sample is selected from a group consisting of a body fluid sample, a tissue sample, a food sample.

8. The method of claim 5, wherein the bacterial species is detected within a time period ranging from about one minute to about one hour.

* * * * *